US012599313B2

(12) United States Patent
Travish

(10) Patent No.: US 12,599,313 B2
(45) Date of Patent: Apr. 14, 2026

(54) HEALTH TRACKERS FOR AUTONOMOUS TARGETING OF TISSUE SAMPLING SITES

(71) Applicant: ViBo Health LLC, Los Angeles, CA (US)

(72) Inventor: Gil Travish, Los Angeles, CA (US)

( * ) Notice: Subject to any disclaimer, the term of this patent is extended or adjusted under 35 U.S.C. 154(b) by 0 days.

(21) Appl. No.: 17/848,154

(22) Filed: Jun. 23, 2022

(65) Prior Publication Data

US 2023/0414125 A1 Dec. 28, 2023

(51) Int. Cl.
*A61B 5/055* (2006.01)
*A61B 5/06* (2006.01)

(52) U.S. Cl.
CPC .............. *A61B 5/055* (2013.01); *A61B 5/064* (2013.01)

(58) Field of Classification Search
CPC ....... A61B 5/055; A61B 5/064; A61B 5/4244; A61B 5/4872; G01R 33/3802; G01R 33/3808; G01R 33/46; G01R 33/4828; G01R 33/383
See application file for complete search history.

(56) References Cited

U.S. PATENT DOCUMENTS

| 7,072,707 | B2 | 7/2006 | Galloway, Jr. et al. | |
| 10,506,943 | B2 | 12/2019 | Kochba et al. | |
| 11,504,021 | B1 * | 11/2022 | Mi ....................... | A61B 6/5217 |
| 2006/0241432 | A1 | 10/2006 | Herline et al. | |
| 2007/0053839 | A1 * | 3/2007 | Zhang ................... | A61B 5/055 |
| | | | | 424/9.1 |

| 2010/0072994 | A1 * | 3/2010 | Lee ....................... | G01R 33/383 |
| | | | | 324/307 |
| 2011/0178388 | A1 * | 7/2011 | Kuhara .................. | A61B 5/055 |
| | | | | 600/411 |
| 2011/0301461 | A1 * | 12/2011 | Anite .................... | A61B 8/4209 |
| | | | | 600/443 |
| 2012/0230566 | A1 * | 9/2012 | Dean .................... | A61B 5/1075 |
| | | | | 382/128 |
| 2014/0105476 | A1 * | 4/2014 | Bulumulla ............ | G06T 11/003 |
| | | | | 382/131 |
| 2014/0107510 | A1 * | 4/2014 | Bogun .................. | A61B 5/316 |
| | | | | 600/523 |
| 2014/0213887 | A1 * | 7/2014 | Reddy ................ | G01R 33/5605 |
| | | | | 600/414 |
| 2014/0350380 | A1 * | 11/2014 | Eidelberg ............... | A61B 6/501 |
| | | | | 600/436 |
| 2015/0301141 | A1 * | 10/2015 | Griswold ........... | G01R 33/5608 |
| | | | | 324/309 |
| 2017/0205478 | A1 * | 7/2017 | Brinker ................ | A61B 5/1077 |

(Continued)

OTHER PUBLICATIONS

Rusu et al., "Segmentation of bone structures in Magnetic Resonance", 2012 (Year: 2012).*

*Primary Examiner* — Adil Partap S Virk
(74) *Attorney, Agent, or Firm* — UCLA Patent Law Clinic

(57) ABSTRACT

Health trackers for targeting tissue sampling sites in accordance with embodiments of the invention are provided. In one embodiment, a health tracker includes: a scanner for capturing spectral data, the scanner comprising: a magnet configured to generate a field gradient across a region of interest; an RF transmitting antenna configured to generate a localized field; and an RF sensing antenna configured to sense a localized area; and where the scanner is configured to obtain magnetic resonance spectral data from predetermined locations with a volume of interest.

14 Claims, 7 Drawing Sheets

(56) References Cited

U.S. PATENT DOCUMENTS

| 2017/0311810 A1* | 11/2017 | Nakamura | A61B 5/4312 |
| 2018/0296103 A1* | 10/2018 | Rege | A61B 5/721 |
| 2018/0329005 A1* | 11/2018 | Sodickson | G01R 33/365 |
| 2019/0076080 A1* | 3/2019 | Prado | A61B 5/4872 |
| 2019/0336017 A1* | 11/2019 | Robinson | A61B 5/1114 |
| 2020/0008676 A1* | 1/2020 | Dong | A61B 5/0035 |
| 2020/0085306 A1* | 3/2020 | To | A61B 5/681 |
| 2020/0367795 A1* | 11/2020 | Qian | A61B 5/681 |
| 2021/0209767 A1* | 7/2021 | Agara Venkatesha Rao | G06T 7/174 |
| 2022/0189195 A1* | 6/2022 | Kabaria | G06V 10/70 |
| 2022/0273184 A1* | 9/2022 | Clark | A61B 5/4082 |
| 2022/0361810 A1* | 11/2022 | Price | A61B 5/7405 |
| 2023/0135351 A1* | 5/2023 | Ravishankar | A61B 5/742 |
| | | | 345/633 |
| 2023/0165569 A1* | 6/2023 | Sonnenschein | G16H 40/67 |
| | | | 600/437 |

* cited by examiner

Scanner 200

210

RF generator

Signal 212
processor

Safety 214
interlocks

Auxiliary
sensor 202
controls

Local
Computer
204

User
Interface
206

216

Calibrations

User 218
Database

Metabolomics
Data 208

201

HEALTH TRACKERS FOR AUTONOMOUS TARGETING OF TISSUE SAMPLING SITES

FIELD OF THE INVENTION

The present invention generally relates to spectroscopy and more specifically to health trackers for autonomous targeting of tissue sampling sites.

BACKGROUND

Nuclear magnetic resonance (NMR) spectroscopy (may also be referred to as magnetic resonance spectroscopy (MRS)) is a spectroscopic technique that may be utilized to observe local magnetic fields around atomic nuclei. For example, a sample may be placed in a magnetic field and the NMR signal may be produced by excitation of a nuclei sample with radio waves into nuclear magnetic resonance that may be detected. NMR or MRS may be used to monitor and diagnose in vivo subjects.

The field of software defined medical diagnosing includes the use of NMR and MRS. Software defined medical diagnosing may refer to the optimization and automation of health monitoring techniques through a combination of software and hardware. The function of this software system is to carry out the automated and interconnected medical diagnostic process to ensure minimal chances of error in diagnostic results.

SUMMARY OF THE INVENTION

The various embodiments of the present health trackers for the autonomous targeting of tissue sampling sites (may be referred to as "health trackers" or "trackers") contain several features, no single one of which is solely responsible for their desirable attributes. Without limiting the scope of the present embodiments, their more prominent features will now be discussed below. In particular, the present device and method for the autonomous targeting of tissue sampling sites will be discussed in the context of smart health tracking. However, the use of autonomous targeting via triangulation for smart health tracking is merely exemplary and various other scanning devices may be utilized for autonomous targeting as appropriate to the requirements of a specific application in accordance with various embodiments of the invention. After considering this discussion, and particularly after reading the section entitled "Detailed Description," one will understand how the features of the present embodiments provide the advantages described here.

One aspect of the present embodiments includes the realization that in current NMR and MRS analysis of live subjects to acquire spectral data, other than the present embodiments, these devices require human intervention to target sampling sites. Spatial encoding refers to determining a position within the volume as a function of resonant frequency and time. Human intervention and spatial encoding approaches limit the search volume and do not enhance signal noise differentiation. For example, standard medical NMR or MRS devices are limited to coded search criteria based on gradients in the magnetic field. Another issue with existing solutions to sample site tracking is they rely on operator intervention or pre-programmed sequences to determine where measurement should be made. Such interactive or pre-set operations are sensible when assessing large, continuous volumes. However, for spectroscopy concerning health tracking, it is not necessary or desirable to acquire tissue spectra across a large volume. The present embodiments solve this problem by autonomously determining sampling sites across a small volume of interest using external sensors to determine the overall region of interest and then determining the tissue type through the process of triangulation. The present embodiments thus advantageously enable autonomous targeting and spectral determination of sampling sub-regions. The present embodiments provide these advantages and enhancements, as described below.

In a first aspect, a health tracker for autonomously targeting tissue sampling sites is provided, the health tracker comprising: a scanner for capturing spectral data, the scanner comprising: a magnet configured to generate a field gradient across a region of interest; an RF transmitting antenna configured to generate a localized field; and an RF sensing antenna configured to sense a localized area; and wherein the scanner is configured to obtain magnetic resonance spectral data from predetermined locations with a volume of interest.

In an embodiment of the first aspect, the RF transmitting antenna comprises phased arrays.

In another embodiment of the first aspect, the health tracker is configured to: determine a search volume within a predetermined region of interest; segment the search volume into a plurality of R-regions; target a plurality of voxels within each of the plurality of R-regions; obtain spectra for each voxel of the plurality of voxels; determine a tissue gradient between a first voxel and a second voxel; and determine a location of a tissue type using triangulation.

In another embodiment of the first aspect, the scanner captures spectral data using nuclear magnetic resonance within the plurality of R-regions.

In another embodiment of the first aspect, the health tracker further comprises an optical detector and wherein the health tracker is further configured to locate the predetermined region of interest using the optical detector.

In another embodiment of the first aspect, the optical detector is a camera.

In another embodiment of the first aspect, the health tracker further comprises a contact sensor and wherein the health tracker is further configured to locate the predetermined region of interest using the contact sensor.

In another embodiment of the first aspect, the triangulation includes: determining a centroid associated with each voxel of the plurality of voxels; assigning a spectral strength for each voxel of the plurality of voxels; and calculating the tissue gradient between the centroids.

In another embodiment of the first aspect, the health tracker is further configured to detect a second tissue type and obtain a tissue gradient for the second tissue type using triangulation.

In another embodiment of the first aspect, the health tracker is further configured to obtain a tissue gradient for each tissue type detected in the plurality of R-regions.

In a second aspect, a method for autonomously targeting tissue sampling sites using a health tracker is provided, the method comprising: generating a field gradient across a region of interest using a magnet of a scanner; generating a localized filed using an RF transmitting antenna of the scanner; sensing a localized area using an RF sensing antenna of the scanner; and obtaining magnetic resonance spectral data from predetermined locations with a volume of interest using the scanner.

In an embodiment of the second aspect, the RF transmitting antenna comprises phased arrays.

In another embodiment of the second aspect, the method further comprises: determining a search volume within a predetermined region of interest using the health tracker; segmenting the search volume into a plurality of R-regions using the health tracker; targeting a plurality of voxels within each of the plurality of R-regions using the health tracker; obtaining spectra for each voxel of the plurality of voxels using the health tracker; determining a tissue gradient between a first voxel and a second voxel using the health tracker; and determining a location of a tissue type using triangulation using the health tracker.

In another embodiment of the second aspect, the method further comprises capturing spectral data using nuclear magnetic resonance by the scanner within the plurality of R-regions.

In another embodiment of the second aspect, the method further comprises locating the predetermined region of interest using an optical detector of the health tracker.

In another embodiment of the second aspect, the optical detector is a camera.

In another embodiment of the second aspect, the method of further comprises locating the predetermined region of interest using a contact sensor of the health tracker.

In another embodiment of the second aspect, the triangulation includes: determining a centroid associated with each voxel of the plurality of voxels; assigning a spectral strength for each voxel of the plurality of voxels; and calculating the tissue gradient between the centroids.

In another embodiment of the second aspect, the method further comprises detecting a second tissue type and obtain a tissue gradient for the second tissue type by triangulation using the health tracker.

In another embodiment of the second aspect, the method further comprises obtaining a tissue gradient for each tissue type detected in the plurality of R-regions using the health tracker.

BRIEF DESCRIPTION OF THE DRAWINGS

The various embodiments of the present device and method for the autonomous targeting of tissue sampling sites will now be discussed in detail with an emphasis on highlighting the advantageous features. These embodiments depict the novel and non-obvious aspects of applying external sensors to determine a search volume of interest followed by the use of triangulation to automatically target and measure tissue spectra to better determine sampling sites. These aspects are shown in the accompanying drawings, which are for illustrative purposes only. These drawings include the following figures.

DETAILED DESCRIPTION OF THE DRAWINGS

Figure 1:
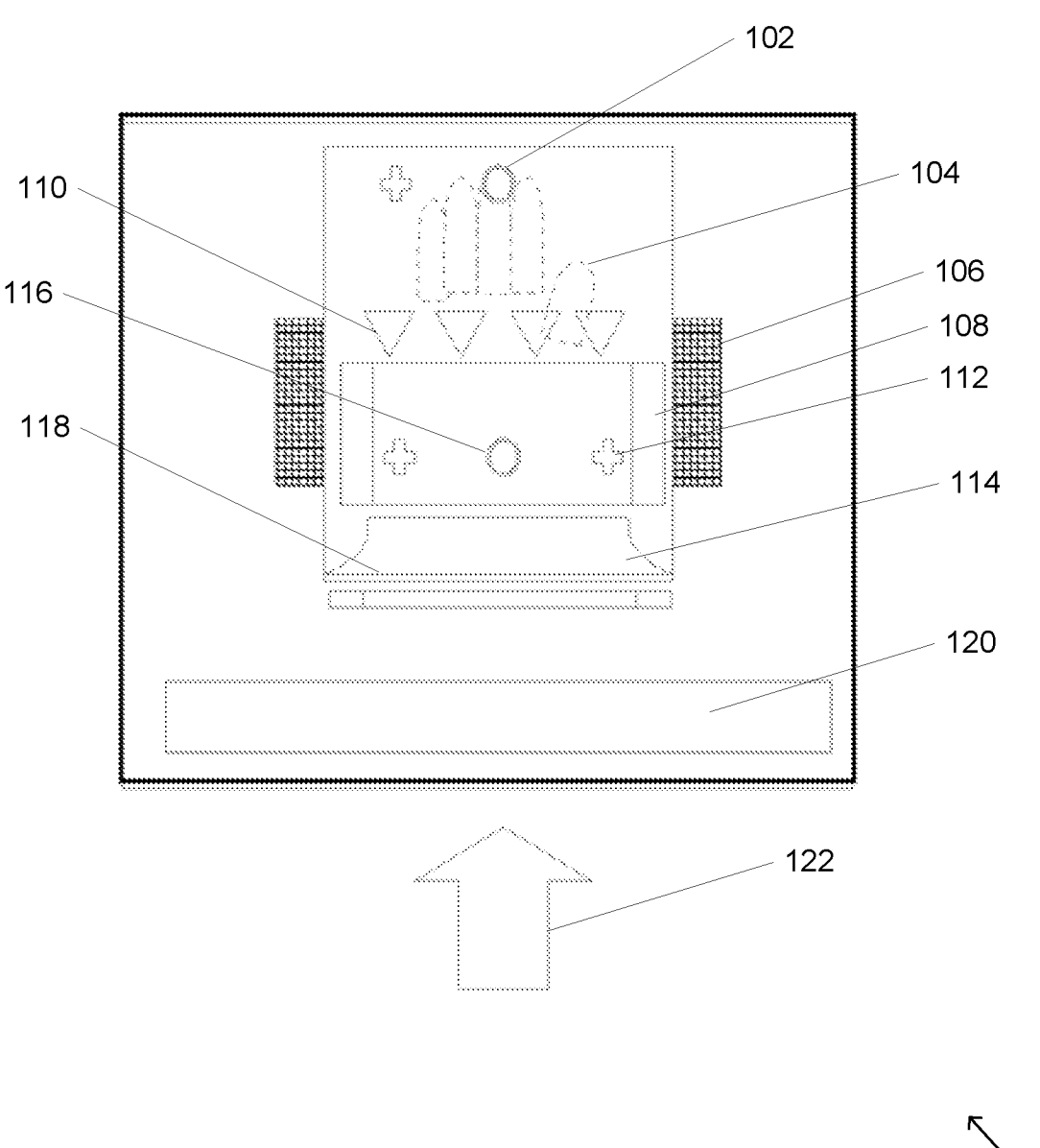
FIG. 1 is a schematic diagram illustrating a scanner of a health tracker in accordance with an embodiment of the invention.

The following detailed description describes the present embodiments with reference to the drawings. In the drawings, reference numbers label elements of the present embodiments. These reference numbers are reproduced below in connection with the discussion of the corresponding drawing features.

Turning now to the drawings, health trackers for the autonomous targeting of tissue sampling sites in accordance with embodiments of the invention are disclosed. In various embodiments, health trackers may include a scanner for capturing spectral data, as further described below. In many embodiments, the scanner may include one or more magnets configured to generate a field gradient across a region of interest. In several embodiments, the scanner may also include an RF transmitting antenna configured to generate a localized field and an RF sensing antenna configured to sense a localized area. In some embodiments, RF transmitting antenna may include phased arrays. In a variety of embodiments, the scanner may be configured to obtain magnetic resonance spectral data from predetermined locations with a volume of interest, as further described below.

Further, in many embodiments, NMR and MRS may be used by the trackers to target, isolate, determine, and/or record tissue spectra. In several embodiments, health trackers may utilize one or more triangulation processes to determine the spectral strength of various tissue types at various target locations. In some embodiments, heath trackers may be based on both magnetic field gradients and RF steering/beam forming. While such an approach is not essential, and other methods of controlling the location of the measurement, the use of magnetic field gradients and/or RF steering/beam forming may reduce complications related to noise from adjacent regions and, in principle, may allow for arbitrarily small sample volumes and control precision.

In many embodiments, processes for automatically acquiring tissue spectra may include utilizing a first set of spectra with a sub-region to determine what types of spectra exist in the region of interest. The processes for automatically acquiring tissue spectra may also include performing calculation(s) to determine a location of a material of interest (e.g., a tissue type). In various embodiments, the processes for automatically acquiring tissue spectra may include a second set of measurements at this optimal location. In a variety of embodiments, the processes for automatically acquiring tissue spectra may be repeated for each material of interest (e.g., tissue type) and within each sub-region. In some embodiments, the processes for automatically acquiring tissue spectra may allow for the possibility that a given material does not exist within a region. Health trackers for autonomous acquiring tissue spectra in accordance with embodiments of the invention are further discussed below.

Health Tracker Designed for Hand Insertion

Health trackers may include scanners to collect biological data from a user. In some embodiments, trackers may include a large-bore (big enough for a user's hand) Nuclear Magnetic Resonance (NMR) spectrometer configured for in vivo measurements in various settings such as, but not limited to, a consumer setting. Various subsystems of scanners are further described below including those aspects that may be distinct from a typical NMR system. In several embodiments, the scanners may include a user interface, allowing users to insert their wrist into the device, automatically aligning their wrist with the sensors, as further described below.

In one application, a scanner is capable of taking in vivo measurements of an individual's hand. A schematic diagram illustrating the scanner of a health tracker in accordance with an embodiment of the invention is shown in FIG. 1. The schematic diagram illustrates a scanner 100 for the autonomous scanning of sampling sub-regions. The scanner 100 may include several subsystems distinct from a traditional NMR scanner. For example, the scanner 100 may include a pulse oximeter 102 that may be configured to measure user blood oxygen content. The scanner 100 may also include a pulse monitor 116 that may be configured to measure a user's heart rate and/or blood pressure.

In reference to FIG. 1, the user may insert their hand according to the extremity insertion direction 122 such that the hand passes through an inspection halo 118 of the scanner 100. If properly positioned, the user's hand should fill a hand rest 104 and the user's arm should be resting in the entrance funnel 114. In many embodiments, the hand rest 104 and the entrance funnel 114 may guide the user's extremity (e.g., hand) to align with the pulse oximeter 102 and pulse monitor 116. The scanner 100 may also include a protective gate 120 that prevents damage to the interior of the scanner. In some embodiments, the protective gate 120 may be configured to readily allow the user's extremity (e.g.,) into the scanning area. The scanner 100 may also include one or more position sensors 112 that may further assess whether the user's hand and/or wrist are in the correct configuration to acquire proper spectral readings, as further described below. In some embodiments, the position sensor(s) 112 may relay correction information to the scanner 100 which may then be used to instruct the user to adjust placement of their hand within the scanner 100.

In reference to FIG. 1, the scanner 100 may also include one or more NMR or MRS monitors 106 to automatically record tissue spectral data (may also be referred to as "spectral data") from an isolated volume of interest, as further described below. In many embodiments, the tissue spectral data may be transmitted using a variety of methods including, but not limited to, wired transmissions, wireless transmissions (e.g., RF transmission) via an antenna 108, etc. In some embodiments, the spectral data may be transmitted to a local computer, user database, and/or the cloud, as further described below. In some embodiments, the scanner may also receive data using a variety of methods including, but not limited to, wired transmission, wireless transmissions (e.g., RF transmission) an antenna 110.

Figure 2:
FIG. 2 is a circuit diagram of a health tracker in accordance with an embodiment of the invention.

As mentioned above, health trackers may include a large-bore NMR spectrometer for in vivo measurements. The health tracker system may be capable of collecting in vivo tissue spectral measurements and transmitting the data, such that a user may access their personal data on a separate device. A circuit diagram of a health tracker in accordance with an embodiment of the invention is shown in FIG. 2. A health tracker 201 may include a scanner 200 connected to various components that may be utilized to receive, transmit, correct, measure, acquire, and/or display spectral data.

In reference to FIG. 2, the scanner 200 may be connected to a signal processor 212 and an RF generator 210 to receive and transmit data from the scanner 200 and interpret feedback signals from a local computer 204 and/or server. The scanner 200 may also be connected to auxiliary sensor controls 202, safety interlocks 214, and remote calibration

216 subsystems that may allow for the maintenance of consistent scanner readings and automatic correction to prevent the determination and collection of inaccurate spectral data. For example, a common issue with software driven medical diagnosing may be having to determine consistent baseline measurements to calibrate future measurements. In many embodiments, the health tracker 201 may be capable of self-calibration such that the process may be automated. In some embodiments, the local computer 204 may also be connected to metabolomics data 208 that may include information regarding metabolites, small molecule substrates, intermediates, and/or products of cell metabolism. For example, the metabolomics data 208 may include small-molecule metabolite profiles that may be utilized in analyzing data generated by the Scanner 200.

In further reference to FIG. 2, there may be a need to register and "log in" a user, keep track of their records, interview them for safety concerns, changes, life events, etc. that inform the measurements, all of which may be recorded in a health dashboard and stored in a user database 218 and/or on the cloud. The interface 206 and/or the scanner 200 may provide feedback such as "hold steady," heartbeat and other real-time feedback is of interest. The signal processing via the signal processor 212 and safety controls via the safety interlocks 214 may be implemented in dedicated hardware. In some embodiments, because of the user interface 206 and the multiple sensors, it may be desirable to have the local computer 204 to handle real-time data management. Various data may be synchronized to the cloud. Such an arrangement may also account for slow internet connections to not impede the ability to take measurements. In some embodiments, the user database 218 (e.g., user accounts, health dashboard) and metabolomic data 208 may be stored in cloud-based services.

Although specific health trackers for acquiring tissue spectra are discussed above with respect to FIGS. 1-2, any of a variety of health trackers for acquiring tissue spectra including various scanners and components as appropriate to the requirements of a specific application can be utilized in accordance with embodiments of the invention. Processes for determining and segmenting volumes of interest in accordance with embodiments of the invention are further described below.

Determining and Segmenting Volume of Interests

A health tracker may autonomously measure the spectral composition of sub-regions to determine sampling sites. For example, in several embodiments, the trackers may automatically target and isolate sampling sub-regions using triangulation. Automatically targeting and isolating sampling sub-regions may greatly improve the speed and efficiency of measurements, as autonomous triangulation may reduce spectral background noise from measurements in a narrower volume of interest than traditional MRS or NMR techniques. In many embodiments, health trackers may locate measurements within the NMR or MRS system based on both magnetic field gradients and RF steering/beam forming. While such an approach may not be essential, and other methods of controlling the location of the measurement may be utilized, the above approach may avoid the complication of noise from adjacent regions and may allow for arbitrarily small sample volumes and control precision.

Figure 3:
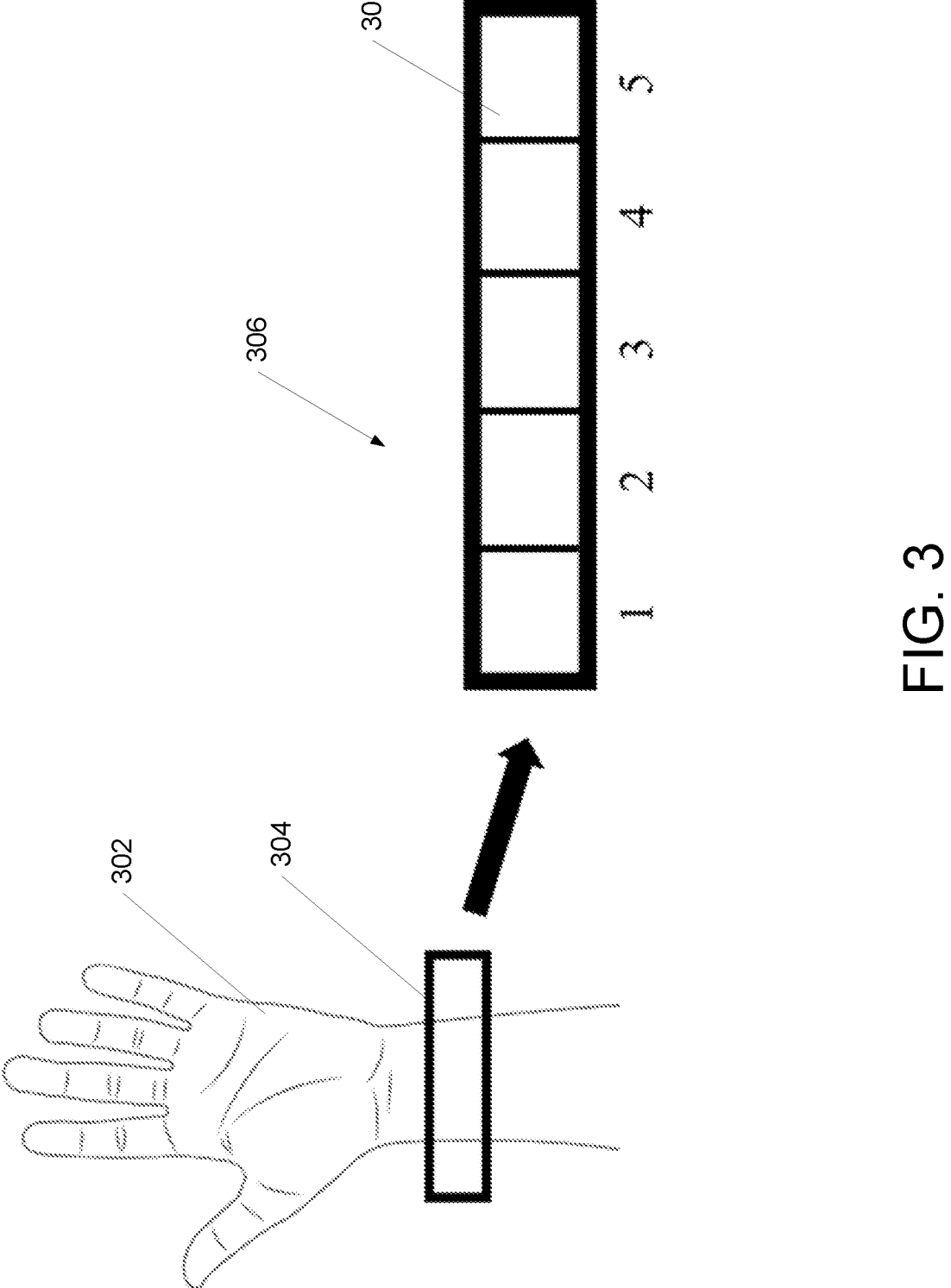
FIG. 3 is a diagram illustrating a process for determining and segmenting a volume of interest of an object (e.g., wrist) in accordance with an embodiment of the invention.

The process of isolating sub-regions within a field of interest and individually measuring material types within each sub-region may be an embodiment for the automatic acquisition of tissue spectra. A diagram illustrating a process for determining and segmenting a volume of interest within a region of interest (e.g., wrist region) in accordance with an embodiment of the invention is shown in FIG. 3. The process may include first isolating a volume of interest 304 within an object 302. The scanner may parse the volume of interest 304 into a plurality of R-regions (sub-regions) 306 which may narrow the search volume. Each individual sub-region 308 may then be isolated for spectral measurements to better determine optimal sampling locations.

Although specific processes for determining and segmenting a volume of interest are described with respect to FIG. 3, any of a variety of processes for isolating sampling sites can be utilized in accordance with embodiments of the invention. Processes for determining spectral compositions of sub-regions in accordance with embodiments of the invention are further described below.

Determining Spectral Compositions of Sub-regions

Figure 4A:
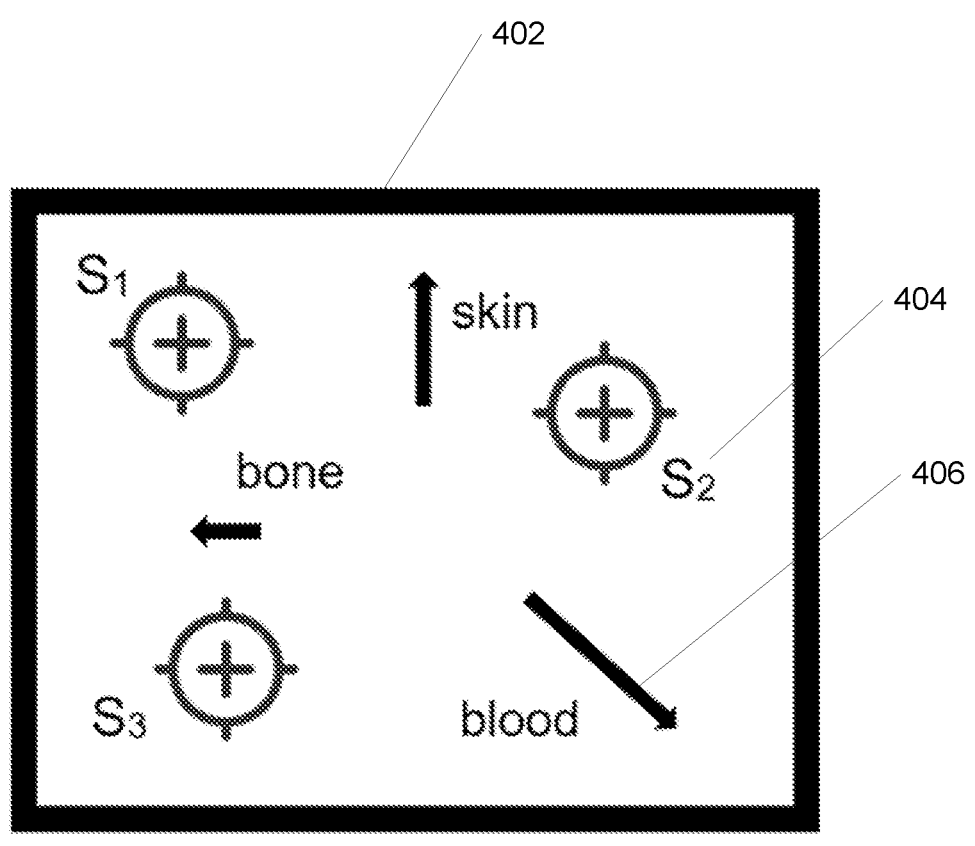
FIG. 4A illustrates a spectral composition of tissue types in an R-region as derived from spectral centroids for three separate voxels (e.g., skin, bone, and blood spectra) in accordance with an embodiment of the invention.
Figure 4A:
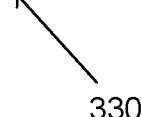
Figure 4B:
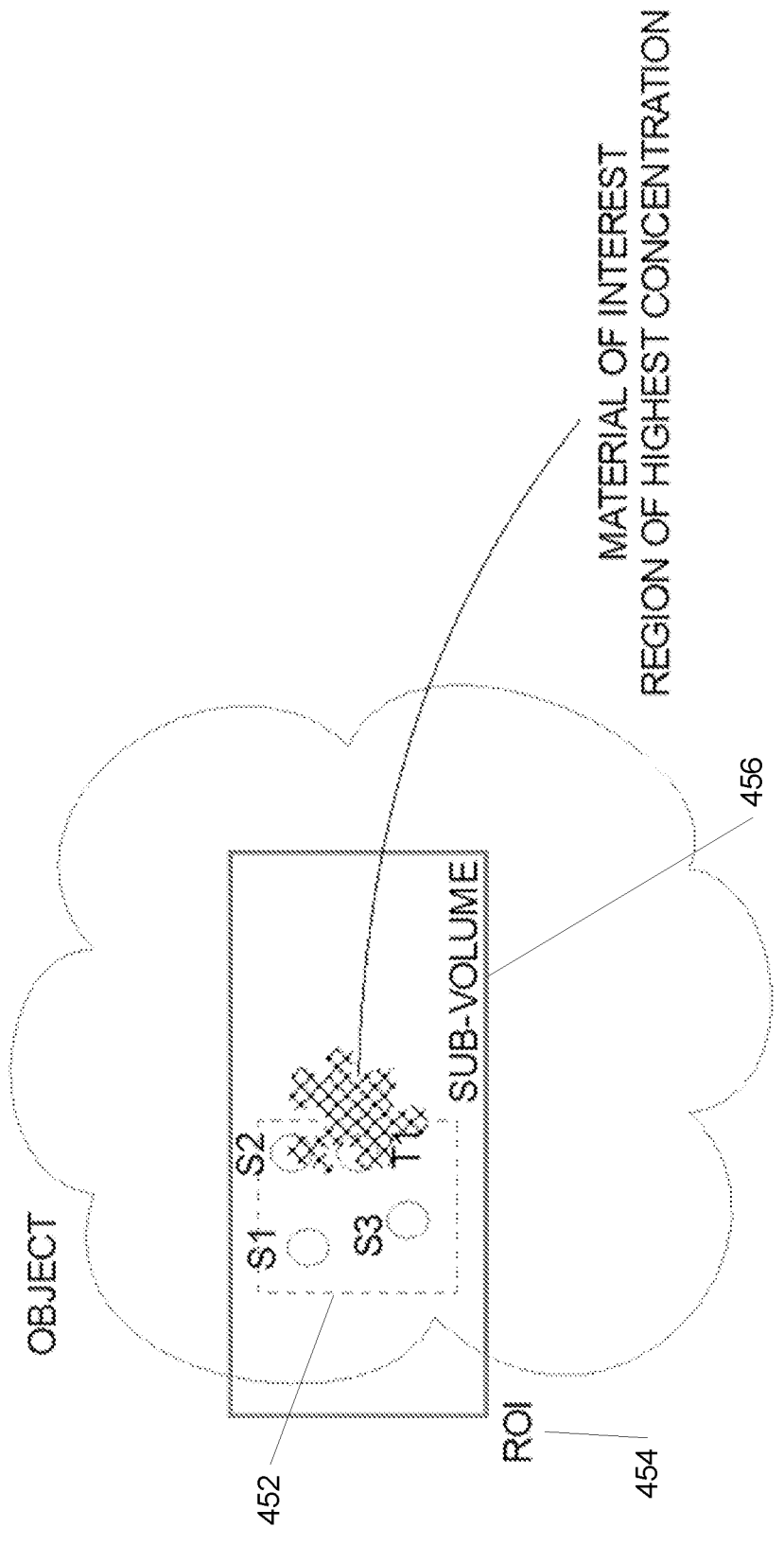
FIG. 4B is a diagram illustrating a process for determining a tissue type within an R-region in accordance with an embodiment of the invention.

In one application, the tissue gradient within a sub-region may be determined based on the amplitude and location of voxel tissue measurements. The tissue gradient may then be used to determine a material (e.g., a tissue type) within a sub-region. FIG. 4A and FIG. 4B illustrate the spectral composition of tissue types in an R-region as derived from spectral centroids for three separate voxels. After determining a sub-region through any of a variety of described embodiments, the scanner may acquire a first set of spectra within the sub-region 402 to better determine which material types are present. This may be followed by a calculation to determine a material of interest 406. A second set of verification measurements may also be taken at the determined optimal location. Materials of interest may include, but are not limited to: blood, skin, bone, muscle, and fat. The first set of spectra may be taken from any of a plurality of sites known as voxels 404 within the sub-region 402. Voxels are units of graphical information that define a point in three-dimensional space. Where pixels have an X and a Y dimensional component, voxels have the added Z dimension. Each voxel provides a location within a sub-region of interest. The process of taking a set of spectra from a plurality of voxels may be repeated for each material of interest detected within a sub-region 402. The process may also allow for the possibility that a given material does not exist within a region, in which case, the material type may not be recorded.

Although specific processes for determining the spectral composition of a sub-region are described with respect to FIGS. 4A and 4B, any of a variety of processes for isolating sampling within a volume of interest can be utilized in accordance with embodiments of the invention. Processes for determining tissue types in accordance with embodiments of the invention are further described below.

Determining Tissue Types

Figure 5:
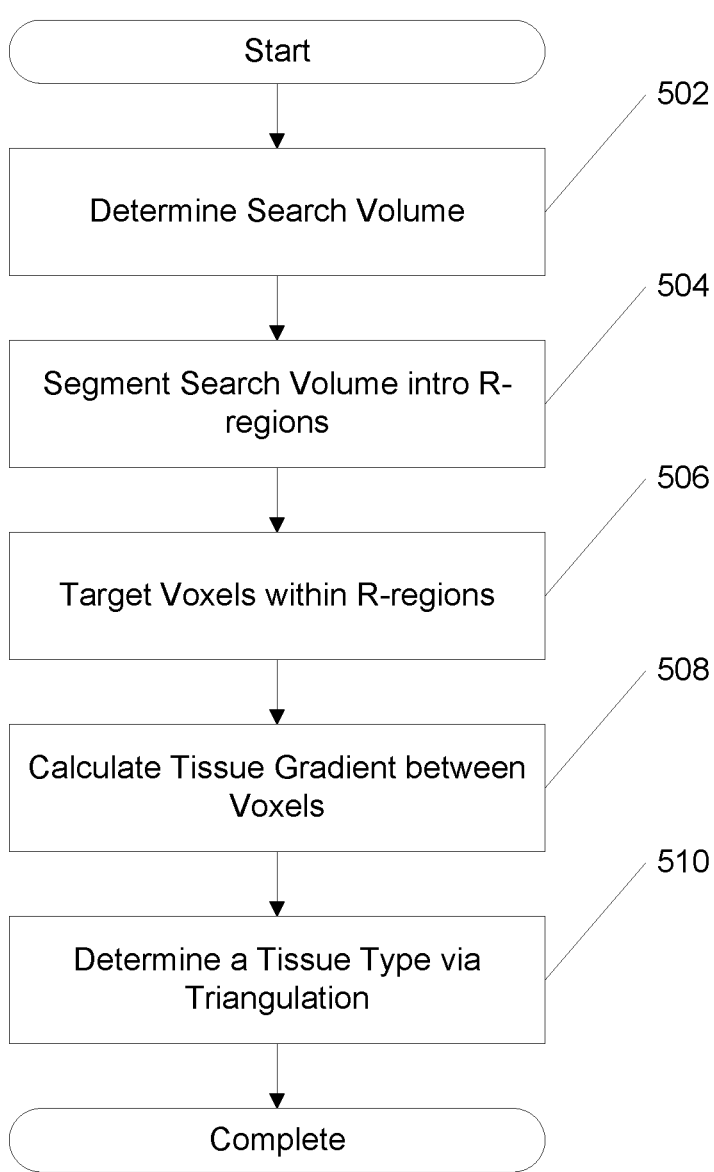
FIG. 5 is a flow chart illustrating a process for autonomously targeting sampling sub-regions and determining a tissue gradient within a sub-region in accordance with an embodiment of the invention.

In another embodiment, the process of determining a material type (e.g., tissue type) may include the segmenting of an object and measuring the tissue type within sub-regions based on the spectral signal from a plurality of voxels. For instance, the flow chart in FIG. 5 illustrates the process for autonomously targeting sampling sub-regions and determining a tissue gradient within a sub-region in accordance with an embodiment of the invention. Steps of this illustration may include the embodiments illustrated in FIGS. 3, 4A, and 4B. A first step may include determining a search volume from the object of interest 502. The object can be a hand or wrist, but may include other objects. Another step may include segmenting the search volume into a plurality of distinct sub-regions 504. Spectral compositions measurements may occur within each sub-region. This may be followed by the targeting of a plurality of voxels within each of the plurality of sub-regions 506. Each voxel may represent a distinct centroid in an X, Y, Z coordinate system. After determining the position and spectral composition of two or more voxels, a later step may include calculating the tissue gradient between one voxel and another voxel for a material type within a sub-region, such that the spectral strength and location of the tissue type may be determined 508. A tissue gradient is a gradual change in the physical properties across biomaterials. Several physical gradients exist in the body, many of which include the transition from one tissue type to another. Examples include bone to ligament or skin to blood. The tissue gradient may be described as the rate this transition occurs, which may be used to extrapolate surrounding tissue types and therefore, map various tissue types across a sub-region. Given a measured tissue gradient, the following step may include determining a tissue type using triangulation 510. Triangulation may refer to any of a variety of triangulation approaches. Examples include a linear approach. The steps described above in accordance with FIG. 5 may be repeated for each subsequent tissue type detected in a sub-region for each of the plurality of sub-regions.

Figure 6:
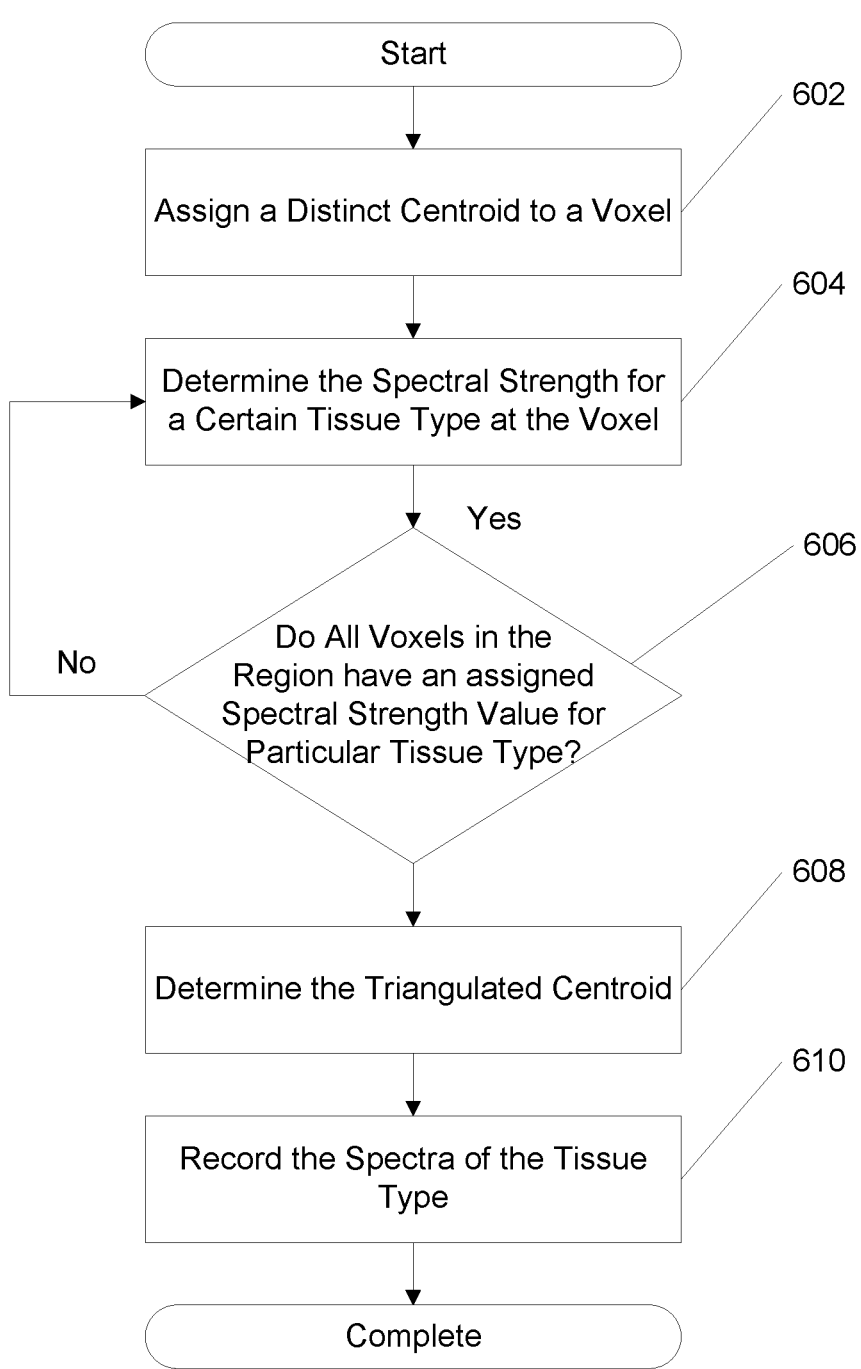
FIG. 6 is a flow chart illustrating the process for calculating tissue gradients and determining the location of the tissue types using triangulation in accordance with an embodiment of the invention.

Determining a material type may be needed to determine viable sampling sites. The determination may be achieved by a variety of processes utilizing the spectral amplitude and location of a tissue type. This may include triangulating the tissue composition of a sub-region based on the spectral signal from a plurality of voxels. FIG. 6 illustrates a process for calculating tissue gradients to determine the location of a tissue type via triangulation. A first step may include assigning a distinct centroid to a voxel within a sub-region 602. The initial centroid provides the three-dimensional coordinate data of the voxel. A later step may then include determining the spectral strength for a certain tissue type at the voxel 604. For a particular tissue type in a sub-region at a particular voxel, the spectral strength may be shown as a single term scaled according to the dimensional components of the initial centroid. This may be further verified by determining whether all voxels within a sub-region have been assigned a spectral strength value for the particular tissue type. If not, the previous steps may be repeated for the remaining voxels in the sub-region. If all voxels have been assigned spectral strength values, then a following step may include determining a triangulated centroid 608. The triangulated centroid may be acquired by calculating tissue gradients between one voxel and another voxel for a set of tissue types (e.g. skin, fat, bone, blood) and repeating this process for each pair of voxels within a sub-region. The triangulated centroid indicates the relative location of a tissue type across a sub-region. An additional step may include recording the spectral measurements for each tissue type detected within the sub-region 610.

Although specific processes for determining a material type are described with respect to FIGS. 5 and 6, any of a variety of processes calculating the spectral composition of a sub-region can be utilized in accordance with embodiments of the invention. While the above descriptions contain many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A health tracker for autonomously targeting optimal tissue sampling sites of a user's hand, the health tracker comprising:

a scanner for capturing magnetic resonance spectral data, the scanner comprising:

an entrance funnel for receiving the user's hand and a hand rest for positioning the user's hand;

a magnet configured to generate a magnetic field gradient across a region of interest of the user's hand;

an RF transmitting antenna configured to generate a localized field; and an RF sensing antenna configured to sense a localized area; and wherein the scanner is configured to capture the magnetic resonance spectral data from optimal tissue sampling sites within the region of interest of the user's hand; and wherein the health tracker is configured to autonomously determine the optimal tissue sampling sites of the user's hand by:

determining a search volume within the region of interest of the user's hand;

segmenting the search volume into a plurality of R-regions to narrow the search volume, wherein the plurality of R-regions comprises a first R-region and a second R-region;

targeting a plurality of voxels within the first R-region, wherein the plurality of voxels of the first R-region comprises a first voxel within the first R-region and a second voxel within the first R-region;

obtaining magnetic resonance spectral data for the first voxel within the first R-region;

obtaining magnetic resonance spectral data for the second voxel within the first R-region; and determining the optimal tissue sampling sites using the magnetic resonance spectra data for first and second voxels within the first R-region.

2. The health tracker of claim 1, wherein the health tracker is further configured to autonomously determine the optimal tissue sampling sites of the user's hand by:

detecting a first tissue type using the magnetic resonance spectra data for the first voxel within the first R-region and the magnetic resonance spectra data for the second voxel within the first R-region;

determining a tissue gradient between the first voxel within the first R-region and the second voxel within the first R-region; and determining a location of the first tissue type using triangulation.

3. The health tracker of claim 2, wherein the scanner captures the magnetic resonance spectral data using nuclear magnetic resonance within the plurality of R-regions.

4. The health tracker of claim 2 further comprising a position sensor and wherein the health tracker is further configured to autonomously determine the optimal tissue sampling sites of the user's hand using the position sensor.

5. The health tracker of claim 4, wherein the health tracker is further configured to assess that the user's hand is in a correct configuration using the position sensor.

6. The health tracker of claim 5, wherein the health tracker is further configured to relay correction information from the position sensor to the scanner, wherein the correction information is used to instruct the user to adjust placement of the user's hand.

7. The health tracker of claim 2, wherein the determining the location of the first tissue type using triangulation includes:

assigning a first centroid to the first voxel within the first R-region and a second centroid to the second voxel within the first R-region;

determining spectral strengths for the first tissue type at the first voxel within the first R-region and for the second voxel within the first R-region;

determining when the spectral strengths of first voxel within the first R-region and the second voxel within the first R-region both have an assigned spectral strength value for the first tissue type; and when determined that the spectral strengths of the first voxel within the first R-region and the second voxel within the first R-region both have the assigned spectral strength value for the first tissue type, determining a triangulated centroid by calculating the tissue gradient between the first and second centroids, wherein the triangulated centroid indicates a relative location of the first tissue type across the first R-region.

8. The health tracker of claim 2, wherein the health tracker is further configured to autonomously determine the optimal tissue sampling sites of the user's hand by:

detecting a second tissue type using the magnetic resonance spectra data for the first voxel within the first R-region and the magnetic resonance spectra data for the second voxel within the first R-region; and determining a second tissue gradient between the first voxel within the first R-region and the second voxel within the first R-region; and determining a location of the second tissue type using triangulation.

9. The health tracker of claim 8, wherein the health tracker is further configured to obtain a tissue gradient for each tissue type detected in the plurality of R-regions.

10. The health tracker of claim 8, wherein the determining the location of the second tissue type using triangulation includes:

assigning a first centroid to the first voxel within the first R-region and a second centroid to the second voxel within the first R-region;

determining spectral strengths for the second tissue type at the first voxel within the first R-region and for the second voxel within the first R-region;

determining when the spectral strengths of first voxel within the first R-region and the second voxel within the first R-region both have an assigned spectral strength value for the second tissue type; and when determined that the spectral strengths of the first voxel within the first R-region and the second voxel within the first R-region both have the assigned spectral strength value for the second tissue type, determining a triangulated centroid by calculating the tissue gradient between the first and second centroids, wherein the triangulated centroid indicates a relative location of the second tissue type across the first R-region.

11. The health tracker of claim 1, wherein the health tracker is further configured to autonomously determine the optimal tissue sampling sites of the user's hand by:

targeting a plurality of voxels within the second R-region, wherein the plurality of voxels of the second R-region comprises a first voxel within the second R-region and a second voxel within the second R-region;

obtaining magnetic resonance spectral data for the first voxel within the second R-region;

obtaining magnetic resonance spectral data for the second voxel within the second R-region; and determining the optimal tissue sampling sites using the magnetic resonance spectra data for first and second voxels within the second R-region.

12. The health tracker of claim 1, wherein the RF transmitting antenna is configured to generate the localized field using RF steering.

13. The health tracker of claim 12, wherein the scanner is configured to obtain the magnetic resonance spectral data from the optimal tissue sampling sites within the region of interest of the user's hand by using the magnetic field gradient across the region of interest generated by the magnet and the localized field generated by the RF transmitting antenna using RF steering.

14. The health tracker of claim 13, wherein the use of the magnetic field gradient and the RF steering reduces complications related to noise from adjacent regions.

* * * * *